United States Patent [19]

Weinberg

[11] Patent Number: 5,096,388
[45] Date of Patent: Mar. 17, 1992

[54] MICROFABRICATED PUMP

[75] Inventor: Marc S. Weinberg, Needham, Mass.

[73] Assignee: The Charles Stark Draper Laboratory, Inc., Cambridge, Mass.

[21] Appl. No.: 497,392

[22] Filed: Mar. 22, 1990

[51] Int. Cl.$^5$ .................. F04B 43/14; F04B 17/00
[52] U.S. Cl. .................. 417/322; 417/413; 417/474
[58] Field of Search .......... 417/322, 412, 413, 474, 417/479

[56] References Cited

U.S. PATENT DOCUMENTS

| | | | |
|---|---|---|---|
| 2,971,471 | 2/1961 | Huebschman | 417/322 |
| 3,264,998 | 8/1966 | Dingman | 417/322 X |
| 4,515,534 | 5/1985 | Lawless et al. | 417/322 |
| 4,911,616 | 3/1990 | Laumann, Jr. | 417/413 |

FOREIGN PATENT DOCUMENTS 2707713 9/1977 Fed. Rep. of Germany ...... 417/322

Primary Examiner—John Rivell
Attorney, Agent, or Firm—Weingarten, Schurgin, Gagnebin & Hayes

[57] ABSTRACT

A micro machined micro pump capable of flow rates on the level of microliters per minute formed by micro machining of a semiconductor material such as silicon with a set of channels or passages and having a semiconductor membrane interacting with the pattern of channels and passages and under selective control of activating means to induce traveling wave type motion of said membrane that creates pump action between inlet and outlet ones of the passages. To induce the pump action motion of the membrane electrical conductors can be applied to the membrane in a pattern which, when selectively activated interact with an electric or magnetic field to produce such motion. Alternatively piezolelectric or other electrostrictive mechanisms may be employed to induce the appropriate membrane motion.

18 Claims, 4 Drawing Sheets

MICROFABRICATED PUMP

FIELD AND BACKGROUND OF THE INVENTION

The present invention relates to small reliable pumps for delivering at relatively low pressure and low flow rates fluids of diverse types. Applications for such pumps include medical implants, miniature scrubbing systems, chemical analysis of very small samples including liquid chromatography and medical diagnosis.

In the past the delivery of very small portions of a fluid material has, for example, utilized small syringes with a plunger digitally controlled by a motor. Such systems possess a number of disadvantages including the requirement of a substantial sample relative to the possible low flow rates; the ability to pump only a discreet sample without interruption for refilling; and relative bulkiness compared to the small quantities delivered.

Present interest focuses on pumping rates at the level or in the general neighborhood of one or more microliters per minute. Being able to deliver such small quantities controllably and reliably for periods of time is an object for the present invention.

SUMMARY OF THE INVENTION

According to the teaching of the present invention a micro fabricated micro pump is provided utilizing selective etching techniques in a block of silicon semiconductor material to produce a plurality of channels including at least an input and an output channel and to provide a semiconductor membrane which is selectively manipulated to produce, in combination with the channels through the semiconductor material, pumping action.

In one embodiment a block of semiconductor material has a substantially planar surface and has formed therein by selective etching techniques at least an inlet and an outlet channel. A membrane of thin etch-formed silicon is placed on the substantially planar surface and has a plurality of selectively actuated current conductors placed across it. A magnetic field runs substantially parallel to the planar surface and orthogonal to the conductors. Selective application of current through the conductors produces a crossed field force upon the membrane which can be controlled to produce a traveling wave effect form of motion which induces a pumping action to deliver fluids along the planar surface from the inlet channel to the outlet channel.

In a further embodiment a plurality of channels are provided in the substantially planar surface and individual separate membranes are provided which are separately activated to emulate a traveling wave pattern and to induce fluid flow along the planar surface in and out of surface channels from an inlet to an outlet channel.

Alternative implementations of the pumping action generating system include electrostatic force effects between separate electrodes and electrode segments on the membrane or piezoelectric or other electrostrictive devices placed upon the membrane and activated to accomplish membrane flexure and a traveling wave effect that generates pumping action.

BRIEF DESCRIPTION OF THE DRAWING

These and other features of the present invention are more fully set forth below in the solely exemplary detailed description and accompanying drawing of which.

DETAILED DESCRIPTION

The present invention contemplates a micro fabricated micro pump utilizing selectively etched semiconductor, quartz or other material and an etch released semiconductor membrane which is selectively deformed in order to produce a pumping effect through the channels.

Figure 1A:
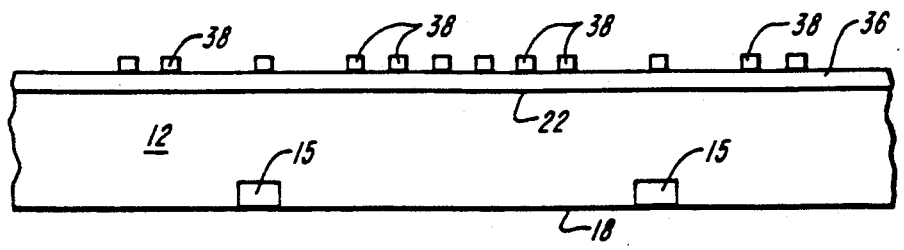
FIGS. 1A and 1B are sectional views of a first embodiment of a micro fabricated micro pump according to the present invention.
Figure 1B:
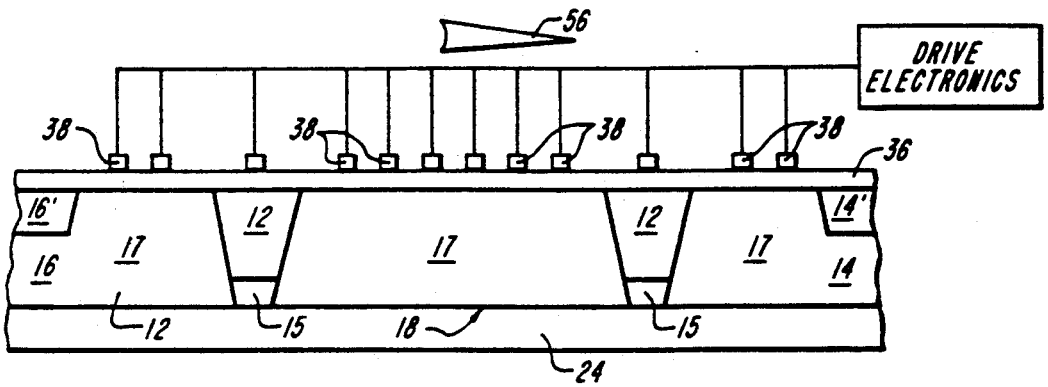

By reference to FIGS. 1A and 1B a first embodiment of the pump of the invention is illustrated. A body 12 of semiconductor material is covered on a first surface 22 with a layer 36 (typically 0.5 to 5 microns) that is to form the flexible membrane shown below. For this purpose, the layer 36 may be doped silicon, oxidized silicon, silicon nitride, polymide, or polysilicon. Each has different properties and different advantages. Materials in tension such as a layer of doped silicon or silicon nitride provide a normally closed condition. Materials in compression, certain oxides and nitrides, and low stiffness material like a polymer allow a peristaltic motion more easily. On the layer 36 is placed a pattern of metalization 38 or other conductors, such as doped polysilicon. Depending on the membrane material, a layer of electrically resistive material may be required between the membranes and the conductors. On a facing surface, bars 15 of diffused dopant, metalizations or otherwise are provided to form etch borders. Depositions may be achieved by diffusion, growth, or CVD.

The silicon 12 is then etched from the side 18 opposite the layer 36, to leave input and output channel areas 14 and 16 and etch pump cavities 17 clear through to the layer 36. To control the etch, an initial doping of regions 14' and 16' above the channel areas 14 and 16 may be used to limit etching. After etching, a cover plate 24 is applied over the etched surface 18 to seal cavities 17 and channels 14 and 16.

Drive electronics 44 sequentially activities conductors 38 for interaction with a magnetic or electric field 56, thereby providing a peristaltic pumping action.

Figure 2A:
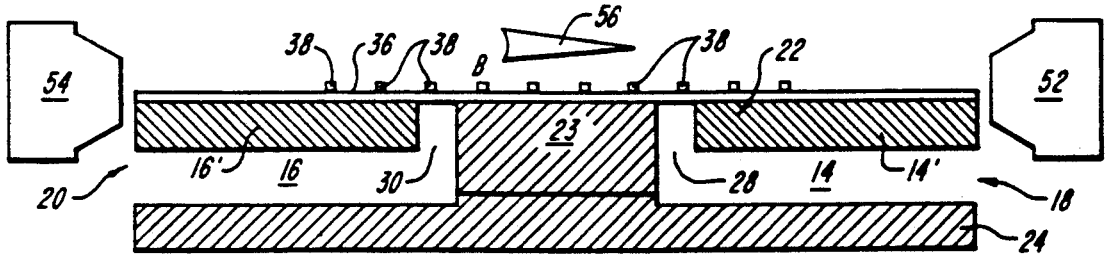
FIGS. 2A and 2B are respective sectional and top views of the pump of a second embodiment.
Figure 2B:
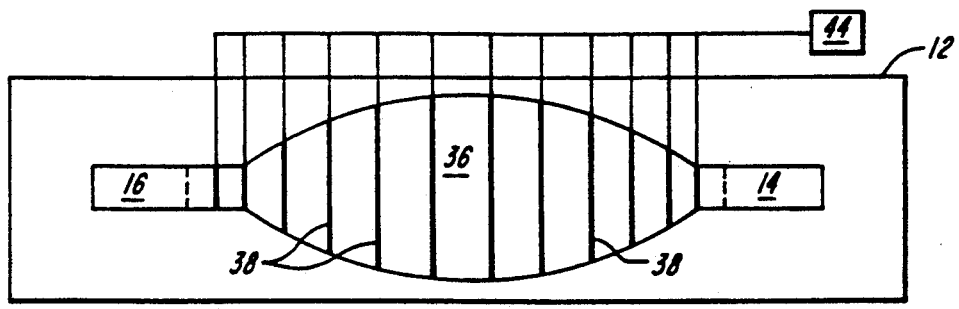

By reference to FIGS. 2A and 2B the features of a further embodiment of the present invention are illustrated in which a central cavity 17 is deleted. A semiconductor block 12 has an inlet channel 14 and an outlet channel 16 formed therein. Cavities 28 and 30 define the upper boundaries of the inlet and outlet channels 14 and 16 in the ends of the channels 14 and 16.

A thin membrane 36 of approximately 0.5 to 5 microns thickness as described above forms a flexible membrane over the surface 22 between cavities 28 and 30 of the channels 14 and 16.

Patterns of conductors 38 are provided over the surface of the membrane 36. As shown in FIGS. 1A and 1B, these are connected to electronics 44 which provides a predetermined pattern of activation for the conductors 38 to interact with magnetic (or electric) field 56.

In the case of a magnetic field 56 it is applied orthogonal to the direction of the conductors 38 by a set of magnetic poles 52 and 54 respectively.

Figure 3A:
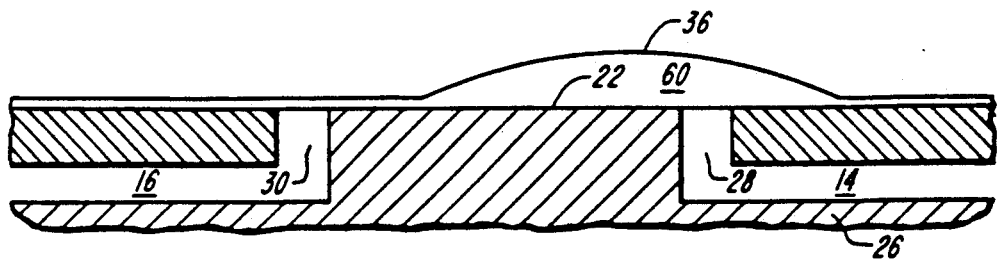
FIGS. 3A, 3B and 3C illustrate the embodiment of FIGS. 2A and 2B in sequential stages of a pumping cycle.
Figure 3B:
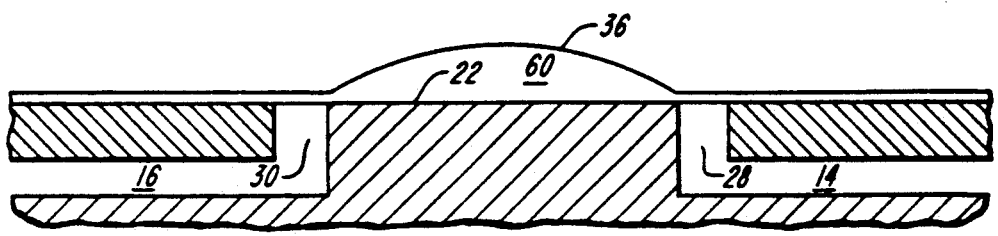
Figure 3C:
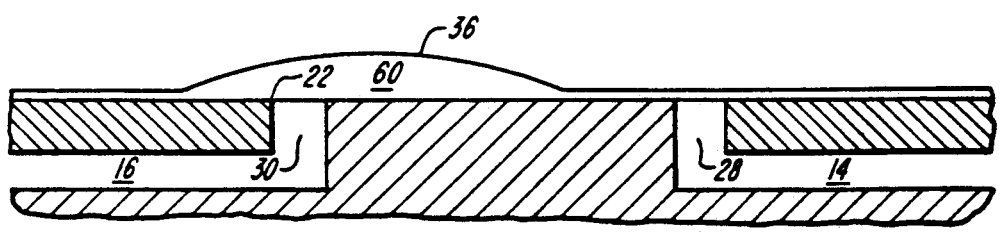

In operation, as illustrated in FIGS. 3A-3C, the conductors 38 are activated in a pattern which produces a traveling wave pattern as indicated for the membrane 36. In particular in FIG. 3A the membrane 36 is selectively forced away from the inlet outlet 14 opening a volume 60 which draws fluid from the inlet into the region above the surface 22. Subsequently, in FIG. 3B, the volume 60 is moved to the left, closing the inlet 14 and moving the trapped volume towards the outlet 16. In subsequent FIG. 3C, the volume 60 is exposed to the outlet channel 16 where it is collapsed by relaxation of the membrane 36 or a repulsion force on the conductors 38 forcing the liquid out. The sequence repeats consecutively producing pumping effects in the microliter per minute range.

The dimensions of the structure of FIGS. 1A, 1B, 2A and 2B and those to follow typically involve a membrane surface area of 500 to 5,000 microns square. The membrane thickness is typically 0.5 to 5 microns and can be any suitable construction, including those recited above.

Figure 4A:
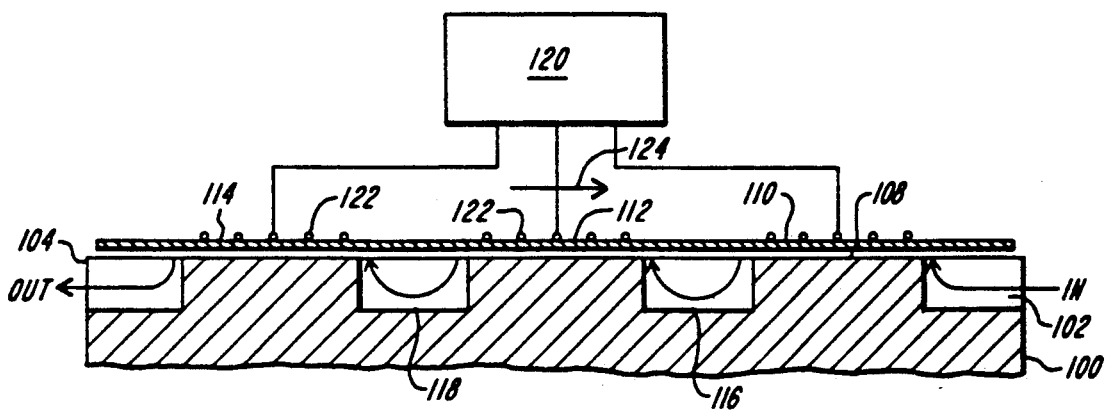
FIGS. 4A and 4B illustrate a further embodiment of the present invention utilizing surface etched channels and independent, separably activated membranes.
Figure 4B:
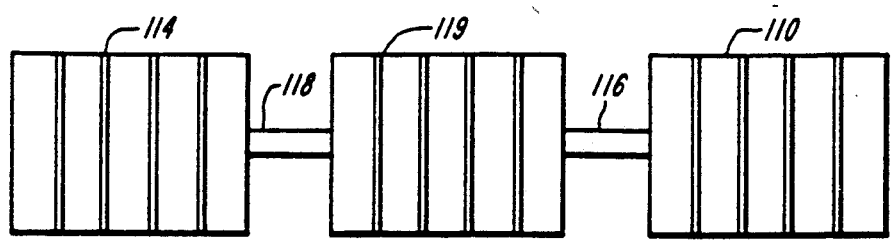

In FIGS. 4A and 4B there is illustrated a further embodiment of the invention in which separate and separately activatable membranes are provided. As shown there a block of semiconductor material 100 is etched with surface channels which form inlet and outlet channels 102 and 104 respectively. Three distinct regions 110, 112 and 114 are located in a surface covering membrane 108 along the flow direction. Additional channels 116 and 118 covered by membrane 108 provide fluid paths between the membranes 110 and 112, and 112 and 114 respectively.

Electrodes 122 are provided across each of the regions 110, 112 and 114 as described above and are activated by electronics 120 in sequential fashion. The current through the conductors 122 driven by the electronics 120 interact with a magnetic (or electric) field 124 as described above. A pumping sequence typically causes the membrane region 110 to be deflected upwards by current passage through conductors 122 thereon inducing fluid from the input conduit 112 into the volume created by the deflection. Simultaneously, the membrane 112 is deflected inducing the flow of fluid into its volume. The membrane 110 is then forced back closing the inlet passage from channel 112 and the membrane 114 is deflected while the membrane 112 is returned to its normal position, forcing fluid out through the outlet passage 104. The membrane 114 is then relaxed completing the output flow and the process repeats.

Figure 5:
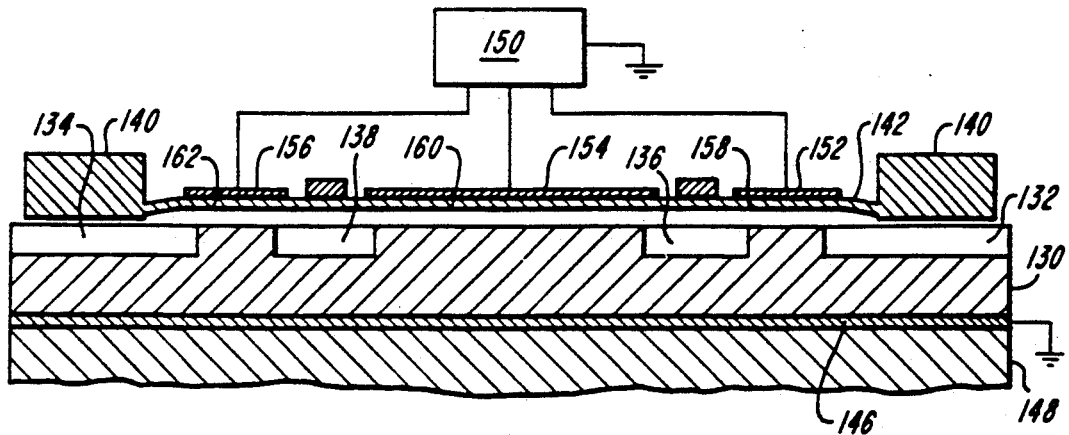
FIG. 5 illustrates a first embodiment of an electrostatically activated pump of the present invention.
Figure 6:
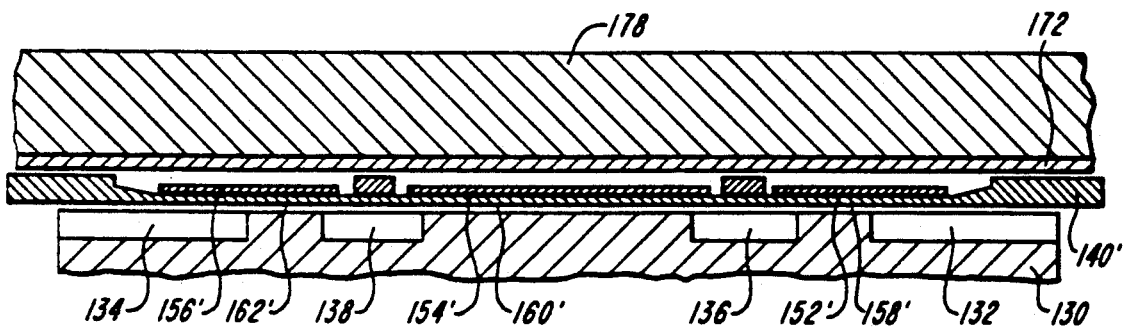
FIG. 6 illustrates a second embodiment of an electrostatically activated pump of the present invention.

FIGS. 5 and 6 illustrate further alternatives of the invention using electrostatic rather than crossed field forces to generate the membrane deflection. As shown in FIG. 5 a block of etched silicon 130 has inlet and outlet channels 132 and 134 and intermediate channels 136 and 138 substantially as illustrated with respect to FIG. 4. An upper frame 140 contains a stretched membrane 142 formed by etching the silicon material of frame 140 to leave only a thinly doped and thus etch resistant membrane portion 142. Stretching is accomplished by boron doping as etch stop. The as stretched membrane 142 provides a normally open valve to the inlet and outlet channels 132 and 134. To provide a facing conductor, the doping of block 130 may be used. Alternatively, the block 130 has buried within it a conducting layer 146 which may be formed by a highly doped layer on a substrate 148 with the block 130 epitaxially grown thereon. Electronics 150 apply electric charge to plated metallizations 152, 154, and 156 on each of respective, separate membranes 158, 160 and 162.

In operation the conducting layer 130 or 146 is connected to circuit common while electrostatic potentials are applied in a selected pattern to platings 152, 154 and 156 to provide the pumping action substantially as illustrated above with respect to FIG. 4.

In FIG. 6 a substantially similar configuration is provided in which a third semiconductor substrate 178 has a conducting layer 172 on a lower planar surface which is brought into approximate relationship to a frame 140' which contains separate membrane segments 158', 160' and 162' which are formed as discussed above but prestretched to provide a normally closed condition for inlet and outlet channels 132 and 134. Segmented electrodes 152', 154' and 156' are activated by electronics, not shown, in association with circuit common potential applied to the overhead electrode 172 to provide the above-disclosed pumping sequence.

Figure 7:
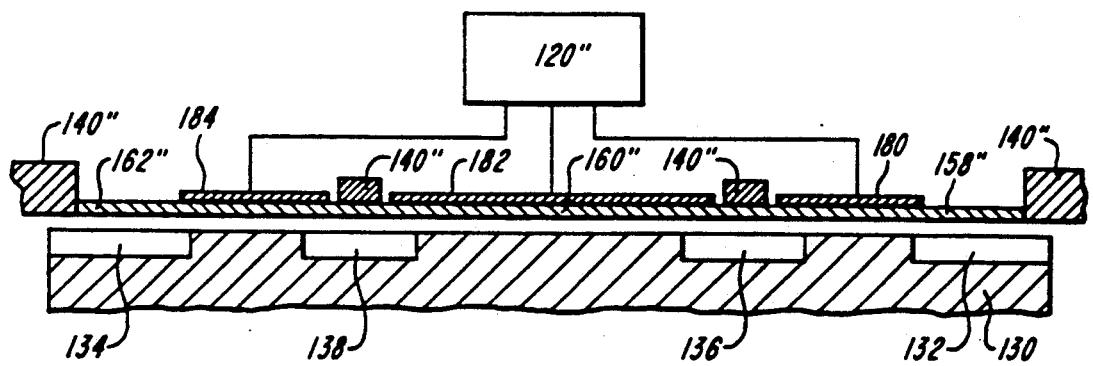
FIG. 7 illustrates an electrostrictively activated embodiment of the present invention.

The force utilized to deflect the membranes may be electrostrictive as illustrated in FIG. 7. As shown there membrane segments 158", 160" and 162" are formed within a semiconductor frame 140" and have over there respective portions electrostrictive elements such as piezoelectric materials 180, 182 and 184. The frame 140" is associated with a silicon block 130 and channels 132, 134, 136, and 138 as described above. Electronics 120" provides activation for each piezoelectric transducer segment 180, 182 and 184 to provide bidirectional motion of the transducer material and accordingly of the membrane 158", 160" and 162" to which they are respectively attached. The bidirectional expansion causes the membranes to deflect upward forming the openings which are controlled in a sequence of deflections to accomplish the pumping action illustrated above.

Figure 8:
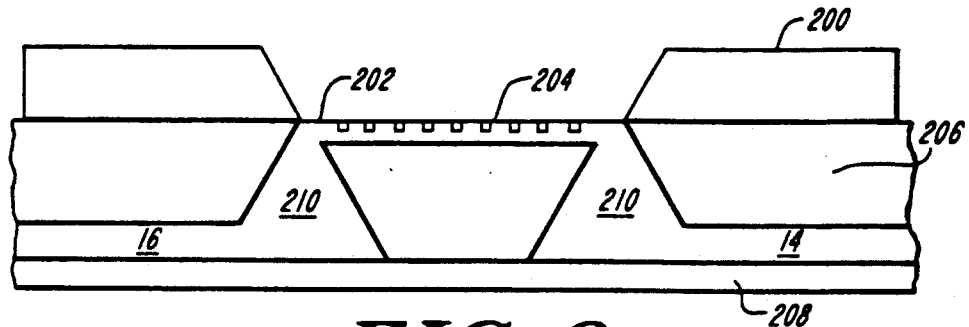
FIG. 8 illustrates a further embodiment with the conductors on the reverse side.

FIG. 8 illustrates another embodiment of the invention in which a silicon wafer 200 is etched to leave a doped, etch stop membrane 202. The area of membrane 202 has conductors 204 deposited on the top surface thereof. When assembled on an etched bottom wafer 206, the conductors 202 face downward. The placement of the conductors on the top is easier than trying to plate into an etched recession. The etched wafer 206 provides, with cover plate 208, input and output channels 14 and 16 and cavities 210.

Figure 9A:
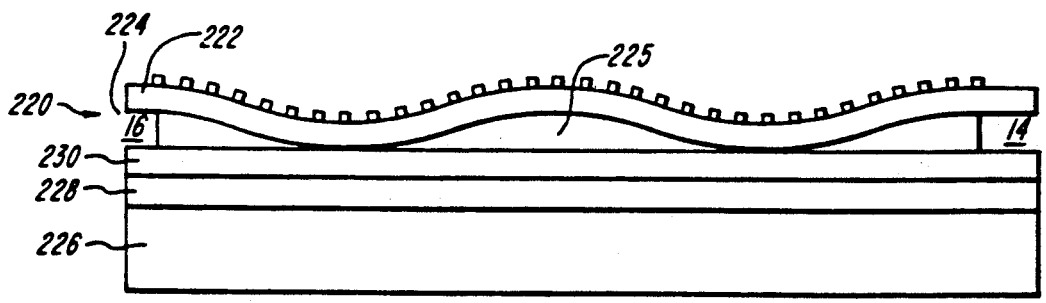
FIGS. 9A and 9B show an embodiment using wave action.
Figure 9B:
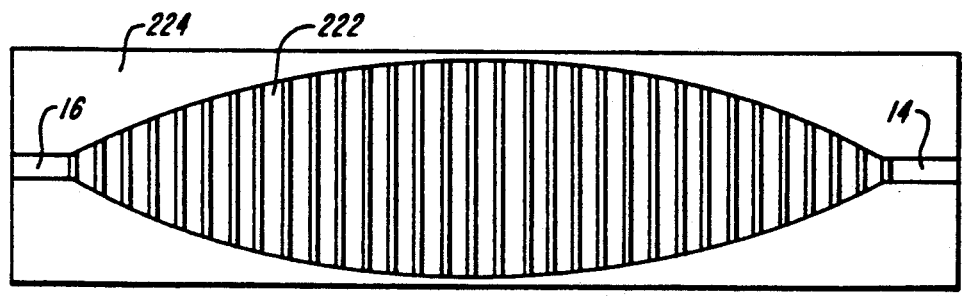

FIGS. 9A and 9B illustrate yet a further embodiment in which a layer of deposited polysilicon forms a thin dome 222 which functions as a top membrane. Similar to FIGS. 1 and 3, pumping is realized by peristaltic deformation of the dome 222. Input and output channels 14 and 16 and pump cavity 225 are shown in FIG. 9. By well known techniques, the dome is formed over a sacrificial layer of glass patterned to define the cavity under the dome 222. After deposition of the polysilicon, the sacrificial layer is removed by selective etchants. The polysilicon dome and glass are deposited on a further silicon wafer 226, the top surface of which has respective oxide and nitride layers 228 and 230.

The above described present invention provides for a compact easily manufactured micro pump capable of long life and high reliability in applications requiring precise control over micro liter scale pumping quantities. Other alternatives to the disclosure above can be realized by those skilled in the art and accordingly it is intended to limit the scope of the invention only as claimed below.

What is claimed is:

1. A micro machined micro pump comprising:
   a body of a chemically etchable material;
   an inlet and an outlet channel through said body from first and second faces terminating in a substantially planar face;
   a membrane over said substantially planar face;
   means for forcing said membrane into shapes which selectively conveys fluid from said inlet passage along said substantially planar face to said outlet passage.

2. The pump of claim 1 wherein said body comprises doped silicon or quartz.

3. The pump of claim 1 wherein:
   said body includes one or more additional channels in said body at said substantially planar face intermediate said inlet and outlet channels;
   said membrane is segmented into selectively controllable portions, with each portion extending across said substantially planar surface between and partially overlapping one and another of said channels.

4. The pump of claim 1 wherein said membrane comprises a thin silicon membrane of 500 to 5,000 microns square.

5. The pump of claim 1 wherein said membrane comprises a stretched semiconductor material biased by stretching to normally cover said inlet and outlet channels.

6. The pump of claim 1 wherein said membrane includes a stretched semiconductor material biased to normally open said inlet and outlet channels.

7. The pump of claim 1 wherein said means for forcing comprises:
   a plurality of electrical conductors placed in a pattern on said membrane; and
   means for sequentially activating said conductors according to a predetermined pattern; and
   means for interacting with said sequentially activated conductors to force said membrane toward or away from said substantially planar surface.

8. The pump of claim 7 wherein said means for interacting includes means for producing a magnetic field in a direction parallel to said substantially planar axially aligned with the direction of flow induced by said forcing means along said substantially planar surface.

9. The pump of claim 7 wherein said interacting means includes means for establishing an electrostatic field with said conductors.

10. The pump of claims 5 or 6 wherein said means for forcing comprises:
    a plurality of electrical conductors placed in a pattern on said membrane; and
    means for sequentially activating said conductors according to a predetermined pattern; and
    means for interacting with said sequentially activated conductors to force said membrane toward or away from said substantially planar surface.

11. The pump of claim 10 wherein said interacting means includes means for electrostatically forcing said pattern of conductors in selective regions.

12. The pump of claim 1 wherein said forcing means further includes:
    a pattern of electrostrictive material on said membrane;
    means for activating said electrostrictive material.

13. The pump of claim 1 wherein said membrane includes a stretched semiconductor material.

14. The pump of claim 1 wherein said membrane is of a material selected from the group consisting of doped silicon, an oxide or nitride of silicon, polysilicon, or a polymide.

15. The pump of claim 1 wherein said body includes a top portion having said membrane in a frame and a bottom portion having said planar surface.

16. The pump of claim 15 wherein said inlet and outlet channels are in said top portion.

17. The pump of claim 15 wherein said channels are in said bottom portion.

18. The pump of claim 1 wherein said planar surface includes a dielectric layer.

* * * * *